United States Patent [19]

McIntyre et al.

[11] 3,955,089

[45] May 4, 1976

[54] AUTOMATIC STEERING OF A HIGH VELOCITY BEAM OF CHARGED PARTICLES

[75] Inventors: Raymond D. McIntyre, Los Altos Hills; Jay D. Wood, Cupertino, both of Calif.

[73] Assignee: Varian Associates, Palo Alto, Calif.

[22] Filed: Oct. 21, 1974

[21] Appl. No.: 516,703

[52] U.S. Cl. .................................. 250/399; 250/385; 250/405; 250/491
[51] Int. Cl.² ......................................... G01K 1/08
[58] Field of Search ............ 250/405, 491, 385, 399

[56] References Cited
UNITED STATES PATENTS

| | | | |
|---|---|---|---|
| 3,612,858 | 10/1971 | De Parry | 250/385 |
| 3,704,284 | 11/1972 | Garmire | 250/385 |
| 3,808,441 | 4/1974 | Boux | 250/385 |
| 3,838,284 | 9/1974 | McIntyre et al. | 250/385 |
| 3,842,279 | 10/1974 | Schumacher | 250/399 |
| 3,845,310 | 10/1974 | Perraudin | 250/385 |
| 3,852,610 | 12/1974 | McIntyre | 250/385 |

Primary Examiner—Harold A. Dixon
Attorney, Agent, or Firm—Stanley Z. Cole; Leon F. Herbert

[57] ABSTRACT

In a high energy X-ray therapy machine, an accelerator accelerates a beam of electrons to energies of several MEV. The electron beam is directed, generally via a beam deflector, onto an X-ray target to produce X-rays for treating a patient. The accelerator and beam deflector are often carried within a rotatable gantry structure, movable for radiating the patient through a series of angular positions or ports. A plurality of ionization chamber radiation detectors are disposed in the radiation field surrounding the beam path of the accelerated electron beam. Ionization current signals are compared from a plurality of the detectors to derive an error signal determinative of a deviation of the beam from an intended beam path. The error signal is utilized to energize beam steering coils for steering the beam along the predetermined beam path. A sample and hold circuit is provided for sampling and holding the error signal to allow interruption of the beam for extended periods of time as may be encountered in the prescribed therapy treatment, while maintaining the proper beam steering conditions.

1 Claim, 9 Drawing Figures

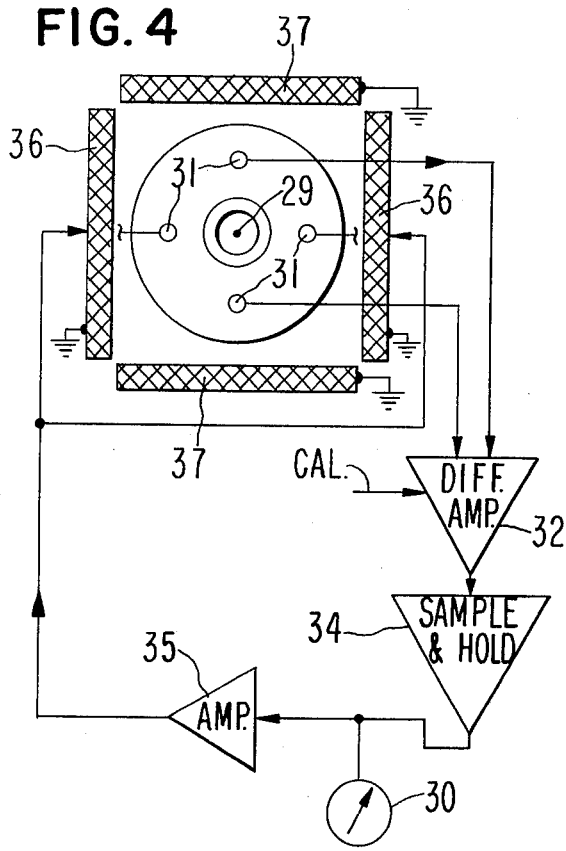
FIG. 4
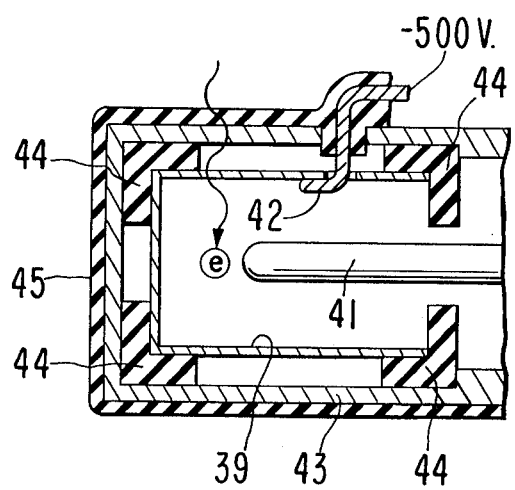
FIG. 5
FIG. 6a
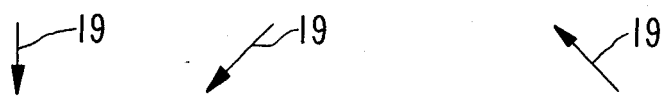
FIG. 6b
$\bar{I}_b$
FIG. 6c
X-RAY INTENSITY
FIG. 6d
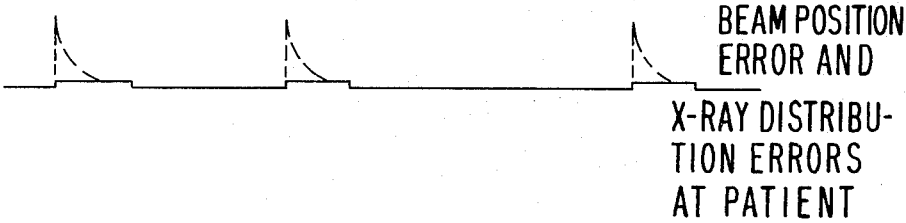
BEAM POSITION ERROR AND X-RAY DISTRIBUTION ERRORS AT PATIENT

AUTOMATIC STEERING OF A HIGH VELOCITY BEAM OF CHARGED PARTICLES

BACKGROUND OF THE INVENTION

The present invention relates in general to automatic steering of high velocity beams of charged particles and more particularly to an improved X-ray or γ-ray therapy machine in which ionization detectors, disposed around the desired beam path, and immersed in the associated radiation field of the beam, give output signals which are employed for steering the beam.

DESCRIPTION OF THE PRIOR ART

Heretofore, the high velocity electron beam of an accelerator, employed in an X-ray therapy machine, has been steered by means of a plurality of semiconductive radiation detectors disposed about the beam path in the radiation field of the beam. The output signals from the various detectors were fed to meters which were compared by the operator so that he could adjust the current through steering coils for steering of the beam along the desired beam path. The problem with this type of beam steering system is that the semiconductive radiation detectors are subject to radiation damage and errors due to temperature drift.

It is also known from the prior art to provide a plurality of beam interceptors placed within the vacuum enclosure around the beam path. The current intercepted by each of the beam interceptors is related to the beam position departure from a desired position. These intercepted current signals were monitored and compared by the operator to derive steering correction signals fed to beam steering coils.

In another prior art system, resonant RF cavities or RF couplings were disposed about the beam path. RF signals were induced in these coupling devices proportional to the beam position. The signals induced in the pickup coils or cavities were compared by the operator and the operator changed the current in steering coils in accordance with the monitored output.

One of the disadvantages of the latter two methods of monitoring the beam position is that the peak beam current amplitude from the detectors is only on the order of a few milliamperes. Therefore, serious signal-to-noise problems are encountered. Furthermore, the RF cavity or coupler method can be utilized only in systems where the beam is accelerated by RF power.

It is also known from the prior art to place a radiation transparent ionization detector of quadrature configuration in the X-ray lobe of an X-ray radiation treatment machine for deriving outputs for automatic steering of the high velocity electron beam over a desired beam path externally of the electron accelerator to the X-ray target. Such a beam steering arrangement is disclosed in U.S. Pat. No. 3,838,284 issued Sept. 24, 1974.

SUMMARY OF THE PRESENT INVENTION

The principal object of the present invention is the provision of an improved system for automatically sterring a high velocity beam of charged particles over a desired beam path within a particle accelerator.

In one feature of the present invention, a plurality of ionization chamber detectors are disposed around the predetermined beam path in the ionizing radiation field surrounding the beam to derive a plurality of ionization current signals proportional to the position of the beam relative to the desired position. Means are included for comparing the detected ionization current signals and so deriving an error signal which is fed to a beam steering means for steering the beam over the desired trajectory within the particle accelerator.

In another feature of the present invention, the error signal employed for energizing the beam steering means is obtained from a sample and hold means which samples and holds the output of the compared ionization current signals, whereby interruption of the beam for substantial periods of time does not adversely affect subsequent automatic steering of the beam.

Other features and advantages of the present invention will become apparent upon a perusal of the following specification taken in connection with the accompanying drawings wherein:

BRIEF DESCRIPTION OF THE DRAWINGS

FIG. 4 is an enlarged view of the structure of FIG. 3 taken along line 4—4 in the direction of the arrows and including electronic circuitry for steering of the beam, FIG. 5 is an enlarged sectional view of a portion of a radiation detector employed in the embodiments of the present invention, and FIG. 6 is a plot of X-ray beam direction, electron beam current, and average X-ray beam intensity $I_R$ versus time, the latter being portrayed with and without the sample and hold circuit.

DESCRIPTION OF THE PREFERRED EMBODIMENTS

Figure 1:
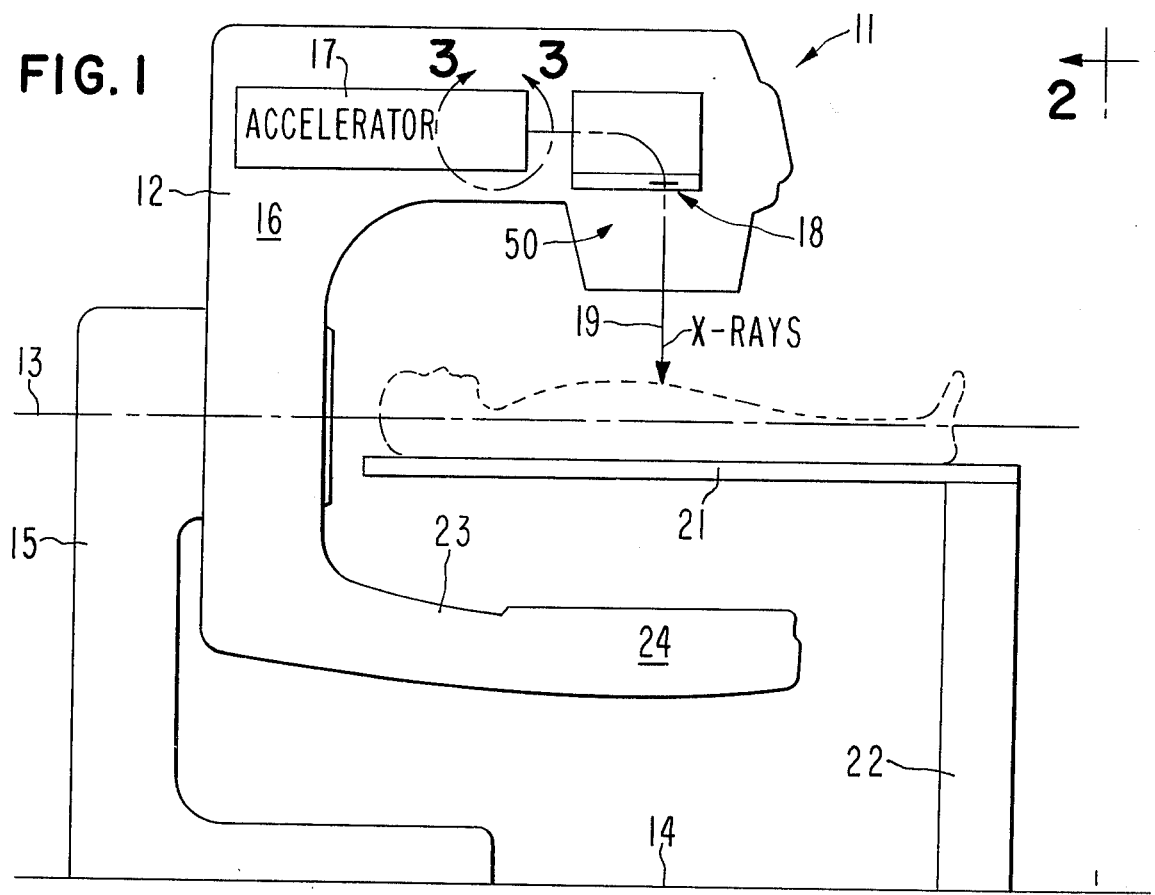
FIG. 1 is a schematic line diagram, partly in block diagram form, of a radiation therapy machine employing features of the present invention.
Figure 2:
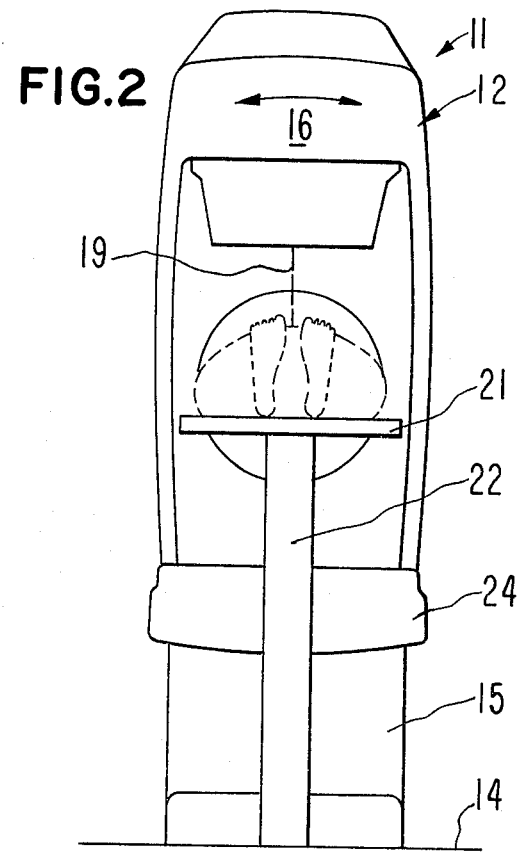
FIG. 2 is an end view of the structure of FIG. 1 taken along line 2—2 in the direction of the arrows.

Referring now to FIGS. 1 and 2 there is shown a typical high energy X-ray therapy machine 11 incorporating features of the present invention. Briefly, the X-ray machine 11 includes generally a rotatable gantry 12 pivotably supported about an axis of revolution 13 from the floor 14 via a pedestal 15. The gantry 12 contains an electron accelerator 17 for accelerating a beam of electrons to relatively high energies, generally within the range e1 to 50 MEV. The electron beam exits the accelerator 17 and passes into an evacuated beam deflection system for directing the beam onto an X-ray target 18 for generating a beam of X-rays 19 which is collimated by a heavy metal structure 50, and then directed onto a patient for radiation therapy purposes. The patient is supported upon a couch 21 supported from the floor 14 via a pedestal 22. The second arm 23 of the gantry 12 in many cases is equipped with an X-ray absorbing structure 24 carried at the end thereof in alignment with the beam of X-rays 19 for absorbing such X-rays incident thereon.

Figure 3:
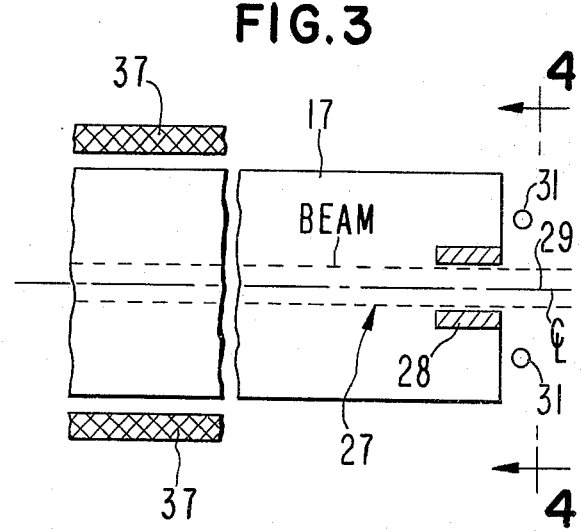
FIG. 3 is an enlarged detailed view of a portion of the structure of FIG. 1 delineated by line 3—3.

Referring now to FIGS. 3 and 4, there is shown the beam steering apparatus of the present invention. More particularly, the beam of accelerated electrons 27 passes axially through the electron linear accelerator 17 and exits from the accelerator 17 by passing through a beam collimator 28 coaxially disposed about the desired beam axis, which is indicated by center line 29. Four quadraturely disposed ionization chamber radiation detectors 31 are disposed around the intended beam path 29 in radially equidistant positions relative to the desired beam axis 29. The outputs from diametrically disposed radiation detectors 31 are fed to the two inputs of a differential amplifier 32 to provide an amplified difference therebetween. A variable DC calibration signal is fed into the differential amplifier 32 for calibrating the output thereof to account for any slight misalignments or offsets in the position or response characteristics of the detectors 31. The difference output signal of differential amplifier 32 is fed to a sample and hold amplifier 34. The output of the sample and hold unit is fed to the input of a power amplifier 35 and to a meter 30 for monitoring of the error signal. The output of the power amplifier 35 is fed to a pair of steering coils 36 disposed on opposite sides of the intended beam path 29 to produce a uniform transverse magnetic field over a region of the beam path 29, preferably in the low velocity region of the accelerator 17, to provide a corrective deflection to the beam so that the beam will exit the accelerator section 17 on the intended beam axis 29. Similarly, the other two radiation detectors 31 are connected to a differential amplifier, sample and hold, and power amplifier (not shown). The amplified error output derived from the second power amplifier is fed to the second (orthogonal) set of beam steering coils 37 for steering the electron beam 27 along the intended beam axis 29.

Referring now to FIG. 5, the ionization chamber radiation detector 31 is shown in greater detail. Briefly, the radiation detector 31 includes an inner cylindrical metallic chamber 39, as of copper, coaxially disposed of a central electrode 41, as of brass. The inner electrode 41 is connected to ground potential through a detector, whereas the outer chamber wall 39 is operated at a negative potential, as of -500 volts, applied thereto via insulated lead 42. The chamber 39 is contained within a metallic housing 43, as of aluminum, via a plurality of insulators 44, as of alumina ceramic. The housing is covered with a suitable insulative potting material as of silicone rubber, at 45.

In operation, photons of ionizing radiation, such as X-rays, are found in a radiation field surrounding the beam and caused by interception of a small portion of the beam on the collimator 28, pass through the housing and inner chamber 39 into the gas fill within the chamber 39 for ionizing same. Upon ionization of the gas fill, an ionization current flows between the inner electrode 41 and the chamber wall 39. This ionization current is detected and fed to one input of the differential amplifier 32. The detected difference or error current is a measure of the assymetry of the radiation field and thus of the beam path relative to the axis 29 of the collimator 28.

Referring now to FIG. 6, there is shown the operation of the sample and hold circuit 34. More particularly, as the direction of the X-ray beam 19 is rotated relative to the position of the patient, as indicated in FIG. 6 a for irradiating the patient through different ports, the accelerator and electron beam will be subjected to different orientations of the earth's field and the perturbations thereof will produce slight unwanted deflections of the electron beam, particularly in the low energy section thereof. Perturbations may also occur due to varying deflection of mechanical support structure at the accelerator due to rotation of the gantry. As the accelerator beam is switched on for patient treatment at different gantry angles, the beam position error will vary. In the absence of error detection means, namely the quadrant set of ion chambers, and associated error correction means, namely the quadrant set of steering coils and driver electronics, substantial loss of accelerator beam may occur at the collimator, with resultant loss of X-ray intensity from the target. In the absence of the sample and hold means, although the desired beam alignment is maintained by the action of the servo means comprised of ion chamber, steering coils, and drive electronics, there will be an unnecessarily large time delay from switch on of the accelerator beam to the stabilized steady state value, due to time constants of the servo loop. The consequent beam alignment errors during this turn on period will produce an adverse radiation treatment distribution within the patient, and this is generally more serious than the variation of intensity during the turn on period. The addition of the sample hold to the drive electronics will greatly reduce the turn on time constant and therefore the treatment errors, particularly in that mode of treatment known as arc therapy, where the gantry rotates around the patient and the accelerator beam is switched on and off so as to maintain a constant preset dose per degree of arc.

The advantages of the use of the ionization chamber detector 31, in accordance with the teachings of the present invention, is that this type of detector yields relatively high signal-to-noise ratio compared to the aforecited prior art (RF and interceptors) and, furthermore, is far less subject to thermal drift and radiation damage than the semiconductor detector means in the aforecited prior art.

What is claimed is:
1. In a radiation generating machine:
means for producing and accelerating a beam of charged particles;
an X-ray target positioned in the path of said beam to generate X-rays for irradiation of a subject;
means for supporting said particle beam producing and accelerating means and for moving said beam producing and accelerating means around a subject to be irradiated and thereby changing the position of said beam producing and accelerating means relative to the direction of a force field of the earth;
means for steering the accelerated beam over a certain predetermined beam path relative to said accelerating means;
secondary emission forming means disposed around the predetermined beam path upstream of the beam relative to said X-ray target for generating a field of ionizing radiation outwardly of the beam when the beam impinges upon said secondary radiation forming means;
ionization chamber detector means disposed around the predetermined beam path for detecting the intensity of the ionizing radiation field generated by said secondary emission forming means, said ionization chamber detector means including chamber means filled with an ionizable medium, and electrode means operatively associated with said chamber means for detecting the ionization current signal flowing within said chamber means as a function of position around said beam due to ionization of the medium fill therein caused by ionizing radiation incident thereon;
means for comparing the detected ionization current signals as a function of position of the beam and for deriving an error signal determinative of the deviation of the beam, if any, from the intended beam path;

said beam steering means being responsive to said error signal for steering the beam along a predetermined beam path; and sample and hold means for sampling and holding the error signal to which the beam steering means is responsive, whereby upon initiation of the beam after interruption of the beam the beam steering means is responsive to the same error signal upon initiation of the beam as it was at the time the beam was interrupted.

* * * * *

UNITED STATES PATENT AND TRADEMARK OFFICE
CERTIFICATE OF CORRECTION

PATENT NO. : 3,955,089
DATED : May 4, 1976
INVENTOR(S) : Raymond D. McIntyre

It is certified that error appears in the above—identified patent and that said Letters Patent are hereby corrected as shown below:

Column 2, line 46, "range el" should read -- range 1 --.

Signed and Sealed this

Twentieth Day of July 1976

[SEAL]

Attest:

RUTH C. MASON
*Attesting Officer*

C. MARSHALL DANN
*Commissioner of Patents and Trademarks*